United States Patent [19]
Sanders

[11] Patent Number: 6,093,209
[45] Date of Patent: Jul. 25, 2000

[54] PROXIMALLY HOLLLOW PROSTHESIS

[75] Inventor: Anthony P. Sanders, Lakeville, Mass.

[73] Assignee: Johnson & Johnson Professional, Inc., Raynham, Mass.

[21] Appl. No.: 09/137,551

[22] Filed: Aug. 20, 1998

[51] Int. Cl.$^7$ ............................................. A61F 2/36
[52] U.S. Cl. ................................................. 623/23.33
[58] Field of Search ........................ 623/18, 19, 20, 623/22, 23

[56] References Cited

U.S. PATENT DOCUMENTS

| | | | |
|---|---|---|---|
| 4,101,985 | 7/1978 | Baumann et al. | 3/1.912 |
| 4,808,186 | 2/1989 | Smith | 623/23 |
| 4,904,262 | 2/1990 | Bensmann | 623/18 |
| 5,047,060 | 9/1991 | Henssge et al. | 623/23 |
| 5,092,899 | 3/1992 | Forte | 623/23 |
| 5,152,798 | 10/1992 | Kranz | 623/23 |
| 5,156,628 | 10/1992 | Kranz | 623/23 |
| 5,316,550 | 5/1994 | Forte | 623/23 |
| 5,330,536 | 7/1994 | Tä ger et al. | 623/23 |
| 5,658,352 | 8/1997 | Draenert | 623/23 |

FOREIGN PATENT DOCUMENTS

| | | | | |
|---|---|---|---|---|
| 0065481 | 11/1982 | European Pat. Off. | | A61F 2/36 |
| 0462357A2 | 9/1991 | European Pat. Off. | | A61F 2/36 |
| 0462357B1 | 9/1991 | European Pat. Off. | | A61F 2/36 |
| 0765644 | 2/1997 | European Pat. Off. | | A61F 2/36 |
| 0765644A2 | 2/1997 | European Pat. Off. | | A61F 2/28 |
| 2611985 | 9/1977 | Germany | | A61F 2/36 |
| 3125657 | 1/1983 | Germany | | A61F 2/36 |

*Primary Examiner*—David J. Isabella
*Attorney, Agent, or Firm*—Nutter, McClennen & Fish, LLP

[57] ABSTRACT

A proximally hollow prosthesis is provided having a cap element and a stem; the prosthesis, in one embodiment, has a cap element suitable to be adapted to a ball and hip socket and has a stem suitable to be implanted in a reamed femoral medullary canal. The stem of the prosthesis has a proximal region and a distal region and is mateable with the cap element of the prosthesis. The proximal region of the stem is open to define a cavity which extends longitudinally a predetermined distance through the proximal region of the stem but not into an isthmus region of the stem, which is located distal to the proximal region of the stem. The distal region of the stem is located distal to the isthmus region of the stem and is made of solid metal or alloys thereof. In another embodiment of the invention, the distal region of the stem is furcated, being at least bifurcated so as to define a plurality of tangs.

8 Claims, 3 Drawing Sheets

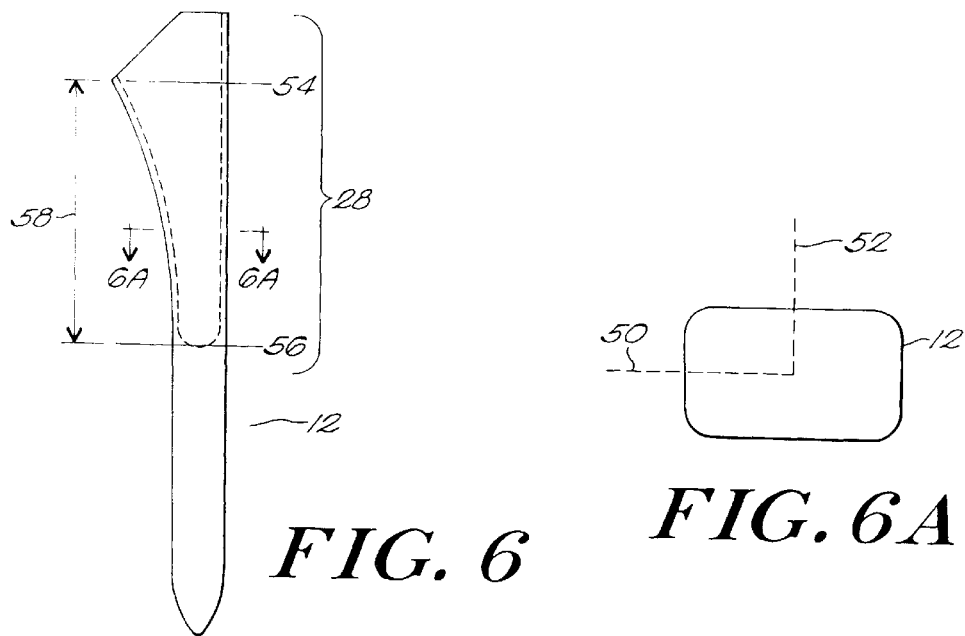
FIG. 6  FIG. 6A
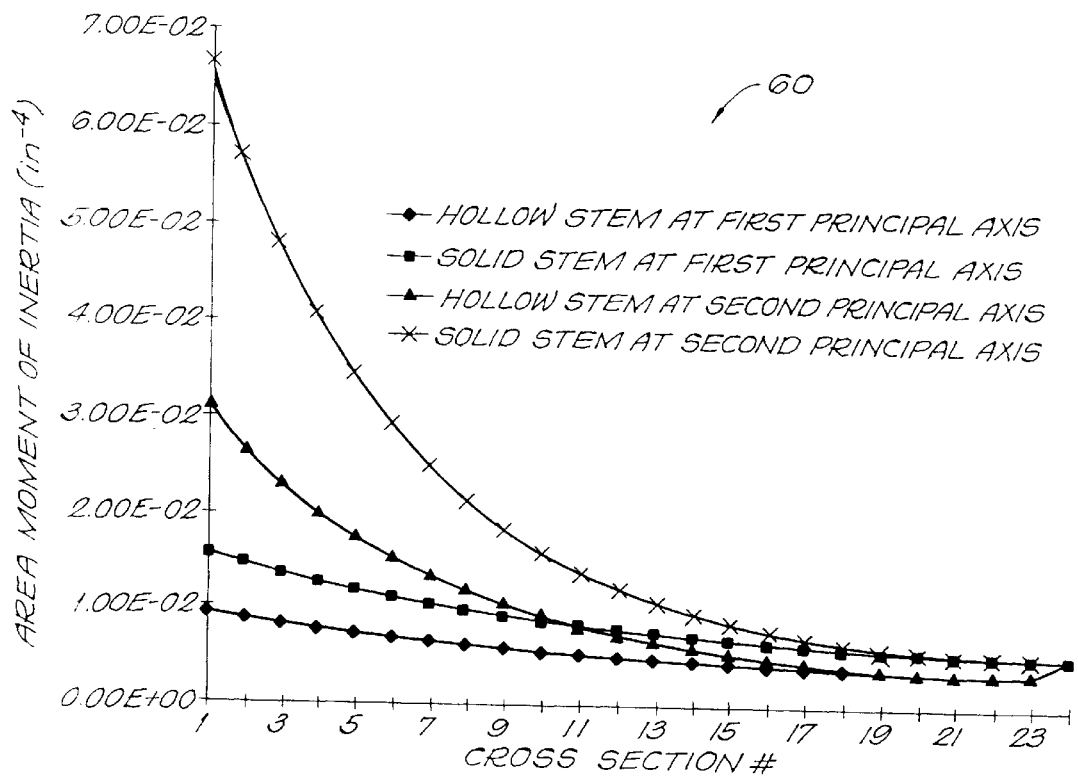
FIG. 7

PROXIMALLY HOLLLOW PROSTHESIS

CROSS-REFERENCE TO RELATED APPLICATIONS

Not applicable.

STATEMENT REGARDING FEDERALLY-SPONSORED RESEARCH

Not applicable.

FIELD OF THE INVENTION

This invention relates to bone prostheses, and more particularly to a proximally hollow hip prosthesis implantable in a reamed femoral medullary canal.

BACKGROUND OF THE INVENTION

Arthroplasty procedures, such as a total hip replacement, can require the removal of the femoral head and neck, followed by implantation of an artificial hip prosthesis into a reamed portion of the femoral medullary canal.

In order to ensure that they are strong and durable, hip prostheses are constructed of metal or alloys thereof. As a result of their metal construction, hip prostheses have a significantly greater stiffness than both the medullary bone canal into which they are implanted and the bone which supports them. Because of this stiffness difference, implanted hip prostheses tend to cause such undesirable effects as cortical bridging or thickening, myositis ossificans and stress shielding.

Stress shielding is an especially undesirable effect of metal hip prosthesis implantation for two reasons. First, stress shielding usually causes associated thigh pain in the implantee. Second, stress shielding can lead, over time, to resorption of the femoral bone which, in turn, can prematurely necessitate the total replacement of a hip prosthesis via a revision process.

Those in the art, in an effort to alleviate the problem of stress shielding arising from an implanted hip prosthesis, have unsuccessfully attempted to provide a hip prosthesis that has bending and strain characteristics such that the bone which supports the implanted prosthesis is able to grow strong while, at the same time, the prosthesis is capable of providing enough structural strength to bear large femoral loads placed upon it for a number of years.

One recent patent, U.S. Pat. No. 5,725,586, describes a bone prosthesis that has a hollow stem. This bone prosthesis, when implanted, is likely to greatly reduce the occurrence of stress shielding because of the increased bending compliance that is provided by its hollow stem.

However, although it works for this intended purpose, the hip prosthesis of U.S. Pat. No 5,725,586 may not provide, due to its design, an optimal amount of structural strength. One of the highest stress concentration points on an implanted hip prosthesis is at the isthmus region of the of the stem of the prosthesis. A hip prosthesis that is either wholly or partially hollow at or distal to the isthmus region of the stem, as is the hip prosthesis of U.S. Pat. No. 5,725,586, may not be strong enough to prevent fracture of the prosthesis at the isthmus region under very large fatigue loads.

Also, a hip prosthesis, such as the one disclosed in U.S. Pat. No. 5,725,586, that is hollow into the distal region of the prosthesis cannot safely allow for the furcation of all or part of its distal region. The prosthesis, if both hollow and furcated in the distal region of the prosthesis, would be especially weak and highly susceptible to an ingress of fluids.

Therefore, it remains a goal in the art to design and implement a hip prosthesis that provides enough structural strength to bear loads that are produced from the hip joint and centered on the femur, and that also provides enough bending compliance to effectively transfer loads and strain to the bone supporting the prosthesis without producing stress shielding and/or other undesired effects.

SUMMARY OF THE INVENTION

The present invention provides a proximally hollow prosthesis to be used primarily as a hip prosthesis in arthroplasty procedures. The hip prosthesis has two principal components, a cap element and a stem; these components are mateable and when mated and implanted in a reamed femoral medullary canal, provide a strong and flexible hip prosthesis that has enough structural strength to bear loads that are produced from the hip joint and centered on the femur while also having enough bending compliance to effectively transfer loads and strain to the bone supporting the prosthesis without producing stress shielding and/or other undesired effects.

The cap element of the prosthesis defines a trunnion at its proximal end and optionally further defines a collar at its distal end. The cap element has a longitudinal axis that extends from its proximal end to its distal end. The cap element also has a neck portion positioned between the trunnion and the collar.

The cap element of the hip prosthesis is mateable with the stem of the hip prosthesis upon the engaging of a mating portion of the cap element to a mating region of the stem such that, upon engaging, the cap element is proximal to the stem. The mating portion of the cap element is a male member and the mating region of the stem is a female member.

The stem of the hip prosthesis has a proximal region, an isthmus region and a distal region wherein the proximal region of the stem has a mating region that can provide a fit between the mating portion of the cap element and the stem. The stem of the hip prosthesis also has a longitudinal axis extending from its proximal region to its distal region. The proximal region of the stem has a longitudinal length and also has a contour which longitudinally tapers. The isthmus region of the stem has a substantially uniform cylindrical contour and a substantially constant cross sectional diameter; the isthmus region of the stem is located between the proximal region of the stem and the distal region of the stem.

The mating region of the proximal region of the stem is female, having an opening which defines a cavity that extends longitudinally through a predetermined portion of the proximal region of the stem. The cavity can have substantially the same longitudinal length as the proximal region of the stem which it affects, but is defined so as to not extend into either the isthmus region of the stem or the distal region of the stem.

The distal region of the stem is located distal to both the cavity and the isthmus region of the stem; the distal region includes a culmination region of the stem. The distal region of the stem has a substantially cylindrical contour such that its cross-sectional diameter is substantially uniform. The cross sectional diameter of the distal region of the stem tapers within the culmination region. The culmination region has a substantially elliptical shape, but can also have a substantially circular, substantially flat or substantially oval shape.

In an alternative embodiment of the present invention, the distal region of the stem is furcated to provide a plurality of independently flexible, resilient tangs.

BRIEF DESCRIPTION OF THE DRAWINGS

A more complete understanding of the present invention and the attendant advantages and features thereof will be more readily understood by reference to the following detailed description when it is considered in conjunction with the accompanying drawings, wherein:

FIG. 6 is an elevational view of the stem of the hip prosthesis of FIG. 1;

FIG. 6A is a sectional view along line 6A–6A of the stem of FIG. 6; and

FIG. 7 is a graphical representation of the area moment of inertia as measured at various transverse cross sections taken through the proximal region of the stem of FIG. 6.

DETAILED DESCRIPTION

Figure 1:
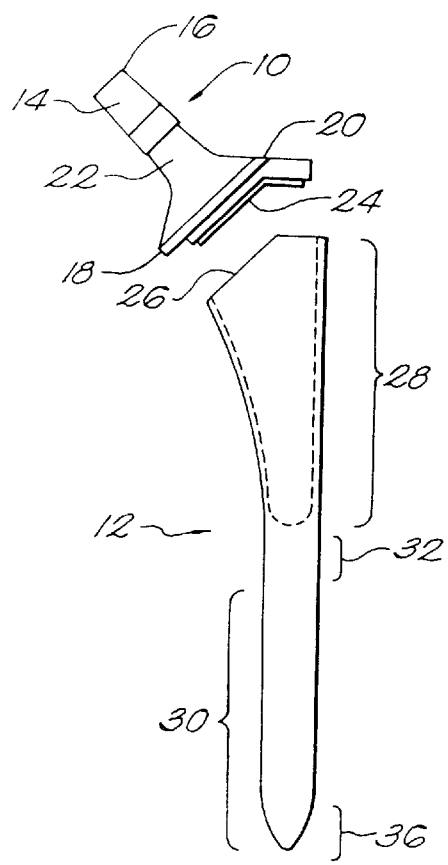
FIG. 1 is an exploded view of a hip prosthesis in accordance with the present invention.

Referring to FIG. 1, a hip prosthesis is shown having as its components a cap element 10 and a stem 12. The cap element 10 defines a trunnion 14 at its proximal end 16 and optionally further defines a collar 18 near its distal end 20. The cap element 10 has a longitudinal axis that extends from its proximal end 16 to its distal end 20. The cap element 10 also has a neck portion 22 positioned between the trunnion 14 and the collar 18 of the cap element.

The cap element 10 of the hip prosthesis is mateable with the stem 12 of the hip prosthesis upon the engaging of a mating portion 24 of the cap element to a mating region 26 of the stem 12 such that upon engaging, the cap element is proximal to the stem. The mating portion 24 of the cap element 10 is a male member and the mating region 24 of the stem 12 is a female member.

The stem 12 of the hip prosthesis has a proximal region 28, a distal region 30 and an isthmus region 32 wherein the proximal region of the stem has a mating region 26 that can provide a fit between the mating portion 24 of the cap element 10 and the stem. The stem 12 of the hip prosthesis also has a longitudinal axis extending from its proximal region 28 to its distal region 30. The proximal region 28 of the stem 12 has a longitudinal length and also has a contour which longitudinally tapers. The isthmus region 32 of the stem 12 has a substantially uniform cylindrical contour and a substantially constant cross sectional diameter; the isthmus region of the stem is located between the proximal region 28 of the stem and the distal region 30 of the stem The mating region 26 of the proximal region 28 of the stem 12 is female, having an opening which defines a cavity 34 that extends longitudinally to a predetermined portion of the proximal region of the stem. The cavity 34 can have substantially the same longitudinal length as the proximal region 28 of the stem 12 which it affects, but is defined so as to not extend into either the isthmus region 32 of the stem or the distal region 30 of the stem.

The distal region 30 of the stem 12 is located distal to the isthmus region 32; the distal region includes a culmination region 36 of the stem. The distal region 30 of the stem 12 has a substantially cylindrical contour such that its cross-sectional diameter is substantially uniform. The distal region 30 of the stem 12 tapers within the culmination region 36. The culmination region 36 of the distal region 30 of the stem 12 is depicted in FIG. 1 as having a substantially elliptical shape, however, the distal region of the stem is specifically contemplated as being capable of supporting a differently-shaped culmination region, including a substantially circular or substantially flat or substantially ovular culmination region.

The stem 12 of the hip prosthesis has a longitudinal length in the range of about 120 millimeters to about 220 millimeters. The female mating region 26 of the stem 12 has dimensions similar enough to those of the male mating portion 24 of the cap element 10 so as to be capable of providing a fit between the cap element and the stem. These dimensions of the mating portion 24 of the cap element 10 and the mating region 26 of the stem 12 can be adjusted, without undue experimentation, to provide for either a reversible or an irreversible fit between the cap element 10 and the stem 12.

The proximal region of the stem 12 extends longitudinally through the stem a distance in the range of about 40 millimeters to about 90 millimeters. The proximal region 28 of the stem 12 is defined as being open so as to further defame a cavity 34 wherein the cavity 34 is defined to extend longitudinally through the proximal region 28 of the stem 12 a distance in the range of about 35 millimeters to about 85 millimeters.

The isthmus region 32 of the stem 12 is located between the proximal region 28 of the stem and the distal region 30 of the stem. The isthmus region of the stem 12 longitudinally extends through the stem a distance in the range of about 10 millimeters to about 30 millimeters and has a generally uniform cross sectional diameter in the range of about 9 millimeters to about 20 millimeters. The isthmus region 32 of the stem 12 is not necessarily related either in placement or shape to an isthmus of a bone or bone canal into which the prosthesis is implanted.

The distal region 30 of the stem 12 is solid and has a substantially uniform cross sectional diameter in the range of about 9 millimeters to about 20 millimeters that longitudinally extends through the stem a distance in the range of about 40 millimeters to about 120 millimeters. The distal region 30 of the stem 12 tapers at its culmination region 36. The culmination region longitudinally extends through the distal region 30 of the stem 12 a distance in the range of about 10 millimeters to about 20 millimeters.

The proximal region 28 of the stem 12 of the present invention has a predetermined wall thickness. This wall thickness of the proximal region 28 of the stem 12 should be at least approximately 1.5 millimeters in order to prevent the stem 12 from buckling under encountered femoral loads. However, the proximal region 28 of the stem 12 should not have a wall thickness of greater than approximately 5.0 millimeters in order for the proximal region 28 of the stem 12 to be sufficiently compliant.

The distal region 30 and the isthmus region 32 of the stem of the present invention also have predetermined wall thicknesses. Although the present invention is capable of including wall thicknesses within and/or among the proximal region 28, the distal region 30 and the isthmus region 32 which may be identical and within the range of about 1.5 millimeters to 5.0 millimeters, because the distal region 30 and the isthmus region 32 of the stem 12 are not hollow, their wall thicknesses may be greater than the wall thickness of the proximal region 28 of the stem 12 and/or be greater than about 5.0 millimeters and still be within the scope of the present invention.

Figure 2:
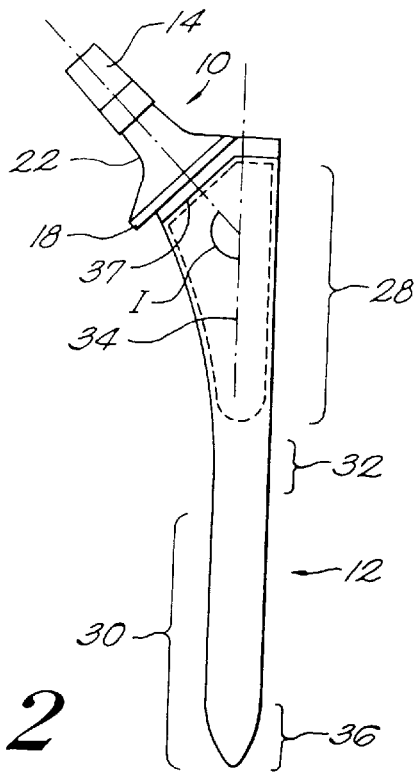
FIG. 2 is an elevational view of the hip prosthesis of FIG. 1 in an assembled configuration.

Referring now to FIG. 2 an assembled hip prosthesis is shown having an identical cap element 10, stem 12 and components thereof to the hip prosthesis of FIG. 1. The cap element 10 and the stem 12 have been mated, wherein the mating portion (not pictured) has been fit into the mating region (not pictured) at a mating area 37. As shown in FIG. 2, the cross sectional diameter of the collar 18 is greater than the cross sectional diameter of any other portion of the cap element 10 or of the stem 12.

While it is generally desired for the collar 18 to have cross sectional dimensions that are greater than the stem 12 and/or the cap element 10 in order to promote a better fit between the cap element and the stem, the collar is not required to have cross sectional dimensions that are greater than that of any of the components of the cap element and/or the stem. Moreover, although not pictured as such in FIG. 2, another portion of the cap element 10 in addition to, or instead of, the collar 18 could have a greater cross sectional diameter than the stem 12. Also, a portion of the stem 12 could have a cross sectional diameter greater than the cross sectional diameter of the cap element 10 or a portion or component thereof.

As is shown in FIG. 2, the cavity 34 in the proximal region 28 of the stem 12 is covered entirely by the cap element 10 when the hip prosthesis is assembled.

The fit between the cap element 10 and the stem 12, although depicted in FIGS. 1–2 as being reversible, can be adjusted to be irreversible without undue experimentation. The fit between the cap element 10 and the stem 12, whether reversible or irreversible, must be tight enough to prevent the ingress of fluids into the stem and/or the dislodging of the cap element from the stem.

Additionally, FIG. 2 depicts the positioning of the cap element 10 in relation to the stem 12 when those components have been assembled to form the hip prosthesis. The positioning is such that the longitudinal axis of the cap element 10 and the longitudinal axis of the stem 12 are not parallel; the intersection of the longitudinal axis of the cap element and the longitudinal axis of the stem forms an inclination angle, I, measuring between about 125° to 140°. This angle can be varied as long as the cap element 10 of the hip prosthesis can properly fit into a ball and socket (not pictured) assembly, and the stem 12 of the hip prosthesis can fit into a reamed femoral medullary canal (not pictured).

Figure 3:
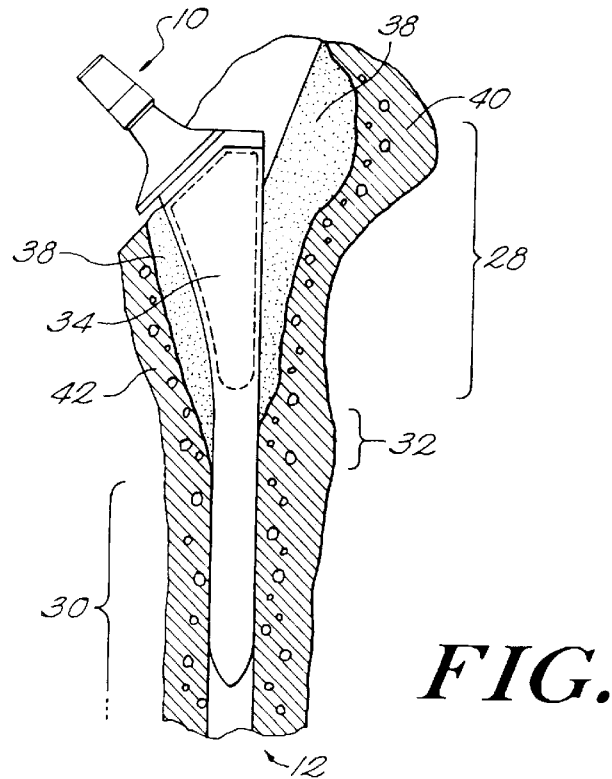
FIG. 3 illustrates the hip prosthesis of FIG. 2 implanted in a reamed femoral medullary canal.

Turning now to FIG. 3, the hip prosthesis of FIGS. 1 and 2 is shown having been implanted in a reamed femoral medullary canal by means of a press fit. The hip prosthesis, although not shown as such, can also be adapted without undue experimentation to be implanted in a reamed femoral medullary canal by other means such as cementing. The proximal region 28 of the implanted stem 12 is surrounded by two layers of bone, an inner layer of soft bone 38 and an outer layer of hard bone. The outer layer of hard bone is, on one side of the stem 12, a trochanter 40 of hard bone, and, on the other side of the stem, a calcar 42 of hard bone. The distal region 30 of the implanted stem 12, as shown in FIG. 3, is surrounded nearly entirely by an outer layer of hard bone. The proximal region 28 and the distal region 30 of the implanted stem 12 may be surrounded by bone in a different manner than that which is illustrated in FIG. 3 while still being in accordance with the present invention.

Because FIG. 3 depicts a hip prosthesis that has been press fit into the reamed portion of the femoral medullary canal, the hip prosthesis may also include means to ensure that the stem 12 remains secure in the femoral medullary canal into which it is implanted. The present invention is capable of being adapted to include means known in the art to maintain a secure press fit of a hip prosthesis within a femoral medullary canal, such means including having a porous and/or beaded coating on the proximal region 28 of the stem 12 which promotes the bony ingrowth of surrounding bone to secure the stem in place. Such means to maintain a secure press fit could also include having a furcated distal region 30 of the stem 12 to anchor the prosthesis in the femoral medullary canal into which it is implanted and/or having spines or flutes at the distal region 30 of the stem 12 to help the stem resist rotation due to torsion forces.

The cavity 34 of the stem 12 of the hip prosthesis has a longitudinal length such that the proximal region 28 of the stem 12 which is affected by the cavity is substantially hollow. Because the stem 12 of the hip prosthesis is substantially proximally hollow, the overall stem contains less of the metal or metal alloys that comprise a non-hollow hip prosthesis and thus has a lower area moment of inertia than an entirely non-hollow hip prosthesis.

Area moment of inertia is related to bending stiffness by the following equation:

$$\text{Bending Stiffness} = (E) \times (I) = (\text{modulus of elasticity}) \times (\text{area moment of inertia})$$

in which the modulus of elasticity is a materials constant equal to the ratio of a material's stress to material's strain. Wherein the modulus of elasticity is a materials constant, the primary factor in determining the bending stiffness of a prosthesis is its area moment of inertia.

A hip prosthesis' bending stiffness is a representation of its ability to transfer femoral loads placed thereupon. An implanted hip prosthesis that has a low bending stiffness will be more flexible and will, therefore, better transfer load to the surrounding bone, which will help to avoid bony remodeling. Because it has a proximally hollow stem, the hip prosthesis of the present invention will have a lower overall area moment of inertia than an entirely non-hollow hip prosthesis and also, therefore, will have a correspondingly lower bending stiffness.

Although it is desirable to have a partially hollow stem of a hip prosthesis in order for the prosthesis to be more flexible, it is not desirable for the stem of the prosthesis to be entirely hollow, nor is it desirable for the hollow region of the stem to coincide with a point of high stress concentration on the stem such as the isthmus region. A stem that is entirely hollow would be compliant and flexible, but also might not be able to withstand large structural loads placed thereupon without promoting fracture of the stem. Also, a hip prosthesis that has a stem with a small hollow region, but wherein that hollow region coincides either wholly or in part with the isthmus region of the stem, could also fracture if large structural loads are placed thereupon.

The hip prosthesis of the present invention, as depicted in FIG. 3, is substantially proximally hollow, having a cavity 34 defined so as to affect only the proximal region 28 of the stem 12. Both the proximal region 28 of the stem 12 and the cavity 34 therein do not coincide with the isthmus region 32 of the stem. The hip prosthesis of the present invention thus incorporates enough hollowness to be compliant, but also includes enough properly-situated metal or metal alloy material to bear the structural loads placed on the prosthesis while and after it is implanted.

Figure 4:
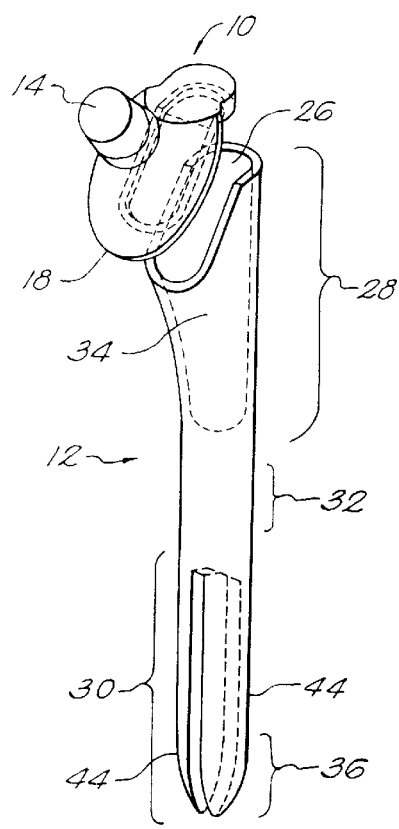
FIG. 4 is a perspective view of an alternate embodiment of the hip prosthesis of the present invention.

Referring now to FIG. 4, an alternate embodiment of the hip prosthesis of the present invention is shown. The hip prosthesis of FIG. 4 is depicted as having a cap element 10, a proximal region 28 of a stem 12 and a cavity 34 that have, respectively, components and measurements that are identical to those of the cap element, the proximal region of the stem and the cavity of the embodiment of the present invention illustrated by FIGS. 1–3. However, the present invention is contemplated as being able to support a cap element 10, a proximal region 28 of a stem 12 and a cavity 34 that are not identical to those of FIGS. 1–3 in either their measurements and/or their components.

The alternate embodiment of the present invention has a distal region 30 of a stem 12 that is furcated. Specifically, FIG. 4 depicts a distal region 30 of the stem 12 that is bifurcated, in that it has two tangs 44. Although not pictured as such, the present invention is capable of supporting a stem 12 with a distal region 30 having more than two tangs 44.

Each tang 44 has a longitudinal length such that the overall longitudinal length of the distal region 30 of the stem 12 is identical or substantially similar to the overall longitudinal length of the distal region of the stem of FIGS. 1–3. Moreover, each tang 44 has a culmination region 36 that is either identical or substantially similar in shape to the culmination region of the entire stem 12 of FIGS. 1–3. However, the distal region 30 of the stem 12 of FIG. 4 can, although not pictured as such, have tangs 44 which have a different longitudinal length and/or have a different shaped or different longitudinal length culmination region than are pictured in FIG. 4. Also, any of the tangs 44 can have a different longitudinal length than any other of the tangs 44 while still being within the scope of the present invention and still allowing the tangs to serve their overall intended purpose.

The tangs 44 of the present invention are depicted in FIG. 4 as longitudinally extending through the distal region 30 of the stem 12 a distance in the range of about 30 millimeters to 80 millimeters and are, while in an unflexed state corresponding to the absence of an applied force or load on the stem 12, uniformly spaced apart from each other a distance in the range of about 3 millimeters to 6 millimeters. Both of these distances are capable of being somewhat modified while still being supported by this embodiment of the present invention.

The tangs 44, while in the unflexed state, must be spaced apart from each other so as to be able to be flexed or "pinched together" similar to a clothespin; this flexing allows for the stem 12 to be compliant and to provide for gradual load transfer from the stem to the femoral medullary canal in which the stem is implanted. This above amount of space that exists between the tangs 44 when the tangs are in the unflexed state is defined as a crotch 46. This crotch 46 acts as a clearance area and affects a constant length of the distal region 30 of the stem 12 as long as the tangs 44 are in an unflexed position as shown in FIG. 4. The tangs 44 will remain in this unflexed position until the introduction of a femoral load on the prosthesis. As femoral load is introduced on the prosthesis and the tangs 44 responsively flex, the clearance area between the tangs 44 is reduced.

The proximal region 28 of the stem 12 of the FIG. 4 has a predetermined wall thickness. This wall thickness of the proximal region 28 of the stem 12 should be at least approximately 1.5 millimeters in order to prevent the stem 12 from buckling under encountered femoral loads. However, the proximal region 28 of the stem 12 should not have a wall thickness of greater than approximately 5.0 millimeters in order for the proximal region 28 of the stem 12 to be sufficiently compliant.

The distal region 30 and the isthmus region 32 of the stem of FIG. 4 also have predetermined wall thicknesses. Although the present invention is capable of supporting wall thicknesses within and/or among the proximal region 28, the distal region 30 and the isthmus region 32 which may be identical and within the range of about 1.5 millimeters to 5.0 millimeters, because the distal region 30 and the isthmus region 32 of the stem 12 are not hollow, their wall thicknesses may be greater than the wall thickness of the proximal region 28 of the stem 12 and still be within the scope of the present invention.

Figure 5:
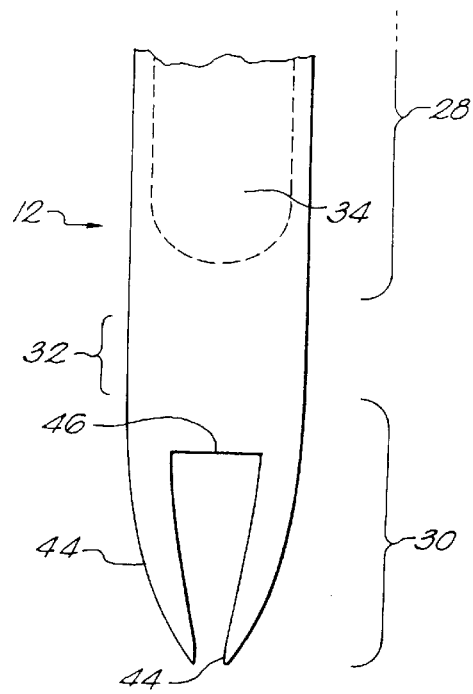
FIG. 5 is a rotated view of the distal region of the hip prosthesis of FIG. 4.

Referring now to FIG. 5, the distal region 30 of the stem 12 of the hip prosthesis of FIG. 4 is shown having been rotated approximately 45°, and having its tangs 44 in a flexed position. The flexed position of FIG. 5 is not a completely flexed position of the tangs 44 as in the completely flexed position, the tangs would be touching each other. The present invention is capable of having tangs 44 which can move interchangeably from an unflexed position to a completely flexed position and to a predetermined number of flexed positions therebetween.

The movement of the tangs 44 from any one position to another is reversible and is in direct response to the encountering of predetermined levels of femoral load. The tangs 44 are also resilient in that once an encountered femoral load has completely subsided, the tangs 44 will return to their unflexed position. However, the tangs 44 can remain at the completely flexed position or any position between the completely flexed position and the unflexed position as long as the femoral load that caused the tangs 44 to flex to that position remains present.

As noted above, although the alternate embodiment of the present invention illustrated by FIGS. 4 and 5 shows two tangs, the present invention could support more than two tangs. Furthermore, the geometry and/or placement of the tangs 44 and the crotch 46 and culmination regions 36 with respect to the distal region 30 of the stem 12 can be somewhat varied without undue experimentation and still be supported by the present invention.

Referring now to FIGS. 6, 6A and 7, as noted above, the primary factor in determining the bending stiffness of a prosthesis is its area moment of inertia; area moment of inertia and bending stiffness are linearly proportional. Graph 60, as depicted in FIG. 7, includes measurements of area moments of inertia of a stem 12 of the hip prosthesis as depicted in FIG. 6 and 6A in accordance with the present invention.

Graph 60 of FIG. 7 is a plot of area moment of inertia measurements at several transverse cross sections taken through a proximal region 28 of a stem 12 in accordance with the present invention. Specifically, these area moment of inertia measurements were calculated with respect to the principal axes of transverse cross sections taken through the proximal region 28 of a stem 12 having dimensions as depicted in FIGS. 6 and 6A, where FIG. 6A shows a transverse cross section taken through the proximal region of a stem having dimensions as depicted in FIG. 6.

A first principal axis 50 and a second principal axis 52 were oriented as shown in FIG. 6A for purposes of calculating the area moment of inertia for the plurality of transverse cross sections taken through the proximal region 28 of a stem 12 of the hip prosthesis of the present invention having dimensions as depicted in FIG. 6.

Overall, twenty-four transverse cross sections, such as the one marked as line 6A in FIG. 6 and shown in FIG. 6A, were taken through a proximal region 28 of a stem 12 of the hip prosthesis of the present invention as depicted in FIG. 6. The first transverse cross section of the proximal region 28 of the stem 12 was taken at line 54 of FIG. 6 and corresponds to cross section number 1 in graph 60. Line 56 of FIG. 6 corresponds to cross section number 24 in graph 60.

The longitudinal distance between lines 54 and 56 of FIG. 6. is noted by reference numeral 58. This distance 58 between lines 54 and 56 was longitudinally subdivided into twenty-two distances, each corresponding to one twenty-second of the distance 58. An area moment of inertia measurement was then calculated, as outlined above, at each of these twenty-two transverse cross sections between lines 54 and 56. These twenty-two area moment of inertia values are provided in graph 60 of FIG. 7, wherein cross section 2 corresponds to the one of these twenty-two distances that is distal to line 54 by a longitudinal length equal to one twenty-second of the distance 58, and wherein cross section 3 corresponds to the one of these twenty-two distances that is distal to line 54 by a longitudinal length equal to two twenty-seconds of the distance 58, and so on.

The area moment of inertia values calculated at each of the principal axes 50, 52 of the twenty-four transverse cross sections taken through the proximal region 28 of the stem 12 having dimensions as depicted by FIG. 6 were plotted on graph 60 of FIG. 7. Also plotted on graph 60 of FIG. 7 were area moment of inertia values for a stem (not shown) that also had identical dimensions to the stem 12 of FIG. 6, but that it was completely solid in its proximal region, isthmus region and distal region. The area moment of inertia values for the completely solid stem were also calculated at each of the same principal axes of twenty-four transverse cross sections taken through its proximally solid region at identical locations as those plotted on graph 60 of FIG. 7 with respect to the stem 12 that has a proximally hollow region 28 as depicted in FIG. 6.

Analysis of graph 60 of FIG. 7 reveals that the area moment of inertia measurements of the completely solid stem are generally higher than the area moment of inertia measurements of the proximally hollow stem at corresponding transverse cross sections. The difference between the area moment of inertia measurements for the proximally hollow stem and the completely solid stem is particularly pronounced with respect to the second principal axis 52.

However, as the transverse cross sections of the proximally hollow and completely solid stems approach the line 56 of FIG. 6 (i.e. —as they rise in number toward 24 on graph 60 of FIG. 7), their area moment of inertia measurements become identical or nearly identical with respect to both the principal axes 50, 52. This similarity in their area moment of inertia measurements is due to the increasing proximity of these transverse cross sections to the non-hollow isthmus and distal regions of the proximally hollow stem of FIG. 6.

Area moment of inertia measurements, as noted above, are the primary factors in determining the bending stiffness of a prosthesis. A low measurement for area moment of inertia will translate to a low bending stiffness and increased compliance of the prosthesis. Graph 60 of FIG. 7 therefore demonstrates that a proximally hollow stem having dimensions as depicted by FIG. 6 will be compliant in proximal portions of its proximally hollow region and structurally strong enough (having a high area moment of inertia and, therefore, a high bending stiffness akin to the values for the completely solid stem in graph 60 of FIG. 7) in its isthmus and distal regions to bear loads placed upon the stem without fracturing.

Moreover, data included in graph 60 of FIG. 7 also demonstrates that a stem having dimensions as depicted in FIG. 6 that is hollow in close proximity to the isthmus region of the stem, a point of high stress concentration in the stem, may have a high enough area moment of inertia (and thus a high enough bending stiffness) at the portions of the proximally hollow region that are in close proximity to the isthmus region of the stem to resist fracture at those regions.

Although FIGS. 6, 6A and 7 correspond to substantially or wholly proximally hollow, non-distally furcated stems, the principles noted above with respect to stems having dimensions as depicted in FIG. 6 and having area moment of inertia measurements in their wholly or substantially proximally hollow regions may also apply to wholly or substantially proximally hollow, distally furcated stems as described with respect to FIGS. 4 and 5 of the present invention. Area moment of inertia measurements taken through transverse cross sections of the proximal region of a substantially or wholly proximally hollow, distally furcated stem should be nearly identical to those provided in graph 60 of FIG. 7 for a substantially or wholly proximally hollow, non-distally furcated stem.

Additionally, although this invention and the embodiments thereof are pictured and described as pertaining to a hip prosthesis, the components and principles of the invention can be applied to other prostheses without undue experimentation. Additionally, although the invention has been shown and described with respect to exemplary embodiments thereof, various other changes, omissions and additions in form and detail thereof may be made therein without departing from the spirit and scope of the invention.

What is claimed is:

1. A hip prosthesis comprising;
   an elongated stem having proximal and distal regions, said stem having a longitudinal axis and a longitudinal length; said proximal region having circumferential wall defining a hollow cavity terminating to an open proximal end and said cavity having a predetermined length entirely within said proximal region of said stem sufficient to allow said stem to flex; and
   a cap element defining a distal collar, an intermediate neck portion and a proximal trunnion, said cap element being configured to mate with said circumferential wall of said open proximal end.

2. The hip prosthesis of claim 1, wherein said circumferential wall has a thickness of at least 1.5 millimeters.

3. The hip prosthesis of claim 1, wherein the cap element is reversibly mated to the open proximal end of the stem.

4. The hip prosthesis of claim 1, wherein the cap element is irreversibly mated to the open proximal end of the stem.

5. The hip prosthesis of claim 1, wherein the stem has a longitudinal length in the range of about 120 millimeters to about 220 millimeters and the proximal region of the stem has a longitudinal length in the range of about 40 millimeters to about 90 millimeters and the longitudinal length of the cavity corresponds to between about 35 millimeters to about 85 millimeters percent of the longitudinal length of the proximal region of the stem.

6. The hip prosthesis of claim 1, further comprising:
   an isthmus region of the stem, located between the proximal region of the stem and the distal region of the stem; and
   a culmination region located in the distal region of the stem.

7. The hip prosthesis of claim 6, wherein the longitudinal length of the isthmus region is between about 10 millimeters to about 30 millimeters and the longitudinal length of the culmination region is between about 10 millimeters to about 20 millimeters.

8. The hip prosthesis of claim 7, wherein said circumferential wall has a thickness no greater than 5.0 millimeters.

\* \* \* \* \*